United States Patent [19]

Spitzer

[11] 3,985,737

[45] Oct. 12, 1976

[54] 3-SULFONATE ESTERS OF CEPHALOSPORIN

[75] Inventor: Wayne A. Spitzer, Indianapolis, Ind.

[73] Assignee: Eli Lilly and Company, Indianapolis, Ind.

[22] Filed: Feb. 6, 1974

[21] Appl. No.: 439,207

[52] U.S. Cl. .............................. 260/243 C; 424/246
[51] Int. Cl.$^2$ ........................................ C07D 501/20
[58] Field of Search ................................ 260/243 C

[56] References Cited
UNITED STATES PATENTS 3,658,799  4/1972  Eardley et al. .................. 260/243 C

*Primary Examiner*—Nicholas S. Rizzo
*Assistant Examiner*—David E. Wheeler
*Attorney, Agent, or Firm*—William B. Scanlon; Everet F. Smith

[57] ABSTRACT

7-Acylamido-3-alkylsulfonyloxy (and phenyl or substituted phenylsulfonyloxy)-3-cephem-4-carboxylic acids and esters thereof are provided via sulfonation of 3-hydroxy-3-cephem esters. The 3-cephem-3-sulfonate esters are useful antibacterial compounds.

11 Claims, No Drawings

3-SULFONATE ESTERS OF CEPHALOSPORIN

BACKGROUND OF THE INVENTION

This invention relates to cephalosporin antibiotic compounds. In particular, it relates to 7-acylamido-3-alkylsulfonyloxy or phenylsulfonyloxy-3-cephem-4-carboxylic acids and esters thereof which are useful antibiotic compounds inhibiting the growth of microorganisms pathogenic to animal and plant life.

Summary

7-Acylamido-3-hydroxy-3-cephem-4-carboxylic acid esters are reacted in an aprotic solvent with $C_1$–$C_6$ alkylsulfonyl halides or phenyl and substituted phenylsulfonyl halides to provide the corresponding 3-alkylsulfonyloxy- or phenyl and substituted phenylsulfonyloxy-3-cephem-4-carboxylic acid esters. The $C_4$ ester group is removed to provide the 7-acylamido-3-$C_1$–$C_6$ alkylsulfonyloxy- (or phenyl and substituted phenylsulfonyloxy) 3-cephem-4-carboxylic acid antibiotic compound.

DETAILED DESCRIPTION

The cephalosporin 3-sulfonate esters of this invention are represented by the following general formula I.

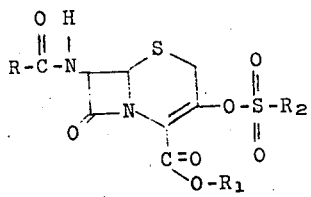

wherein R is $C_1$–$C_6$ alkyl, $C_1$–$C_3$ haloalkyl, $C_1$–$C_3$ cyanoalkyl, phenyl, methylphenyl, hydroxyphenyl, halophenyl, nitrophenyl, aminophenyl, methoxyphenyl, 4-amino-4-carboxybutyl, or a 4-substituted-amino-4-carboxybutyl ester group of the formula

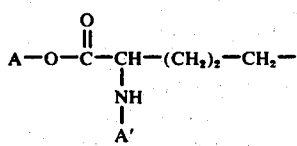

wherein A is diphenylmethyl, p-nitrobenzyl, benzyl, 2,2,2-trichloroethyl, t-butyl, or p-methoxybenzyl and A' is $C_2$–$C_4$ alkanoyl, $C_2$–$C_4$ haloalkanoyl, benzoyl, halobenzoyl, 2,4-dinitrophenyl, or phthaloyl; or R is a group of the formula

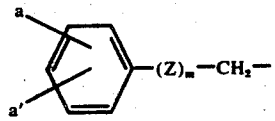

wherein $a$ and $a'$ independently are hydrogen, $C_1$–$C_4$ lower alkyl, $C_1$–$C_4$ lower alkoxy, halogen, hydroxy, nitro, amino, or carboxy;
Z is O or S; and
$m$ is 0 or 1;

or R is a group of the formula

P—CH—
    |
    Q wherein P is 2-thienyl, 3-thienyl, phenyl or a substituted phenyl group of the formula

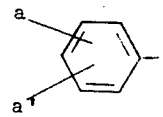

wherein $a$ and $a'$ are as defined above, Q is hydroxyl, formyloxy, acetoxy, carboxy, sulfo, amino or protected amino;
or R is a group of the formula

R'—CH$_2$— wherein R' is 2-thienyl, 3-thienyl, 2-furyl, 2-oxazolyl, 2-thiazolyl, or 1-tetrazolyl;
$R_2$ is $C_1$–$C_6$ alkyl, phenyl, halophenyl, $C_1$–$C_3$ lower alkylphenyl, or nitrophenyl;
$R_1$ is hydrogen, benzyl, 4-methoxybenzyl, 4-nitrobenzyl, diphenylmethyl, 2,2,2-trichloroethyl or t-butyl; and when $R_1$ is hydrogen the pharmaceutically acceptable non-toxic salts thereof.

In the foregoing definition of the compounds provided by this invention, the term "$C_1$–$C_6$ alkyl" refers to the straight and branched chain alkyl hydrocarbon groups such as methyl, ethyl, n-propyl, isopropyl, n-butyl, sec-butyl, n-amyl, isoamyl, n-hexyl, and the like; "$C_1$–$C_3$ cyanoalkyl" refers to such groups as cyanomethyl, 2-cyanoethyl, 3-cyanopropyl, and 2-cyanopropyl; "$C_2$–$C_4$ alkanoyl" refers to acetyl, propionyl, butyryl, and the like; "$C_2$–$C_4$ haloalkanoyl" refers to chloroacetyl, bromoacetyl, 2-chloropropionyl, 3-bromobutyryl, and the like; "$C_1$–$C_4$ lower alkyl" refers to the straight and branched chain lower alkyl hydrocarbon groups such as methyl, ethyl, n-propyl, iso-propyl, n-butyl, t-butyl, and the like; "$C_1$–$C_4$ lower alkoxy" refers to methoxy, ethoxy, isopropoxy, n-butoxy, and the like. As used herein, the term "halogen" refers to fluoro, chloro, bromo, and iodo. The term "halobenzoyl" refers to the chloro and bromo substituted benzoyl groups such as 4-chlorobenzoyl, 4-bromobenzoyl, 2,4-dichlorobenzoyl, and the like.

Illustrative of the groups in the above definition represented by the following formula where $m$ is 0 are

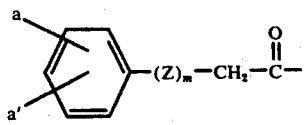

phenylacetyl, 4-methylphenylacetyl, 3-ethylphenylacetyl, 4-isopropylphenylacetyl, 2-methylphenylacetyl, 4-chlorophenylacetyl, 4-nitrophenylacetyl, 4-bromophenylacetyl, 2,4-dichlorophenylacetyl, 3-bromophenylacetyl, 4-iodophenylacetyl, 2-fluorophenylacetyl, 3,4-dihydroxyphenylacetyl, 4-hydroxyphenylacetyl, 3-hydroxyphenylacetyl, 2,6-dimethoxyphenylacetyl, 3-carboxyphenylacetyl, 4-aminophenylacetyl, 3-ethoxyphenylacetyl, 4-methoxyphenylacetyl, 3,4-dimethoxyphenylacetyl, 4-t-butoxyphenylacetyl, 2-carboxyphenylacetyl, 3-chloro-4-methylphenylacetyl, 3-nitrophenylacetyl, and the like. When in the above formula $m = 1$ and Z represents —O—, illustrative groups are the following. Phenoxyacetyl, 4-hydroxyphenoxyacetyl, 3-hydroxyphenoxyacetyl, 4-chlorophenoxyacetyl, 3-bromophenoxyacetyl, 3-ethylphenoxyacetyl, 4-methylphenoxyacetyl, 3-hydroxy-3-methylphenoxyacetyl, 4-aminophenoxyacetyl, 3-nitrophenoxyacetyl, 2-carboxyphenoxyacetyl, 2-chlorophenoxyacetyl, 4-t-butylphenoxyacetyl, 4-methoxyphenoxyacetyl, 3,4-dimethoxyphenoxyacetyl, 2-aminophenoxyacetyl, 4-isopropoxyphenoxyacetyl, 4-nitrophenoxyacetyl, and like acyl groups. When in the foregoing formula $m = 1$ and Z represents —S—, illustrative groups are the following. Phenylmercaptoacetyl, 4-chlorophenylmercaptoacetyl, 3-hydroxyphenylmercaptoacetyl, 3,4-dimethylphenylmercaptoacetyl, 4-aminophenylmercaptoacetyl, 3,4-dichlorophenylmercaptoacetyl, 3-bromophenylmercaptoacetyl, 4-fluorophenylmercaptoacetyl, 2,6-difluorophenylmercaptoacetyl, 4-nitrophenylmercaptoacetyl, 3-fluorophenylmercaptoacetyl, and like groups.

When in the formula I R is a 4-substituted-amino-4-carboxybutyl group,

is representative of esterified amino-protected adipoyl groups wherein the ester group is diphenylmethyl, p-nitrobenzyl, benzyl, p-methoxybenzyl, 2,2,2-trichloroethyl, or t-butyl, and the substituted amino groups can be acetamido, propionamido, chloroacetamido, benzamido, 2,4-dichlorobenzamido, 4-bromobenzamido, phthalimido, 2,4-dinitroanilino, and the like.

When in formula I R represents a group of the formula

illustrative acyl groups, R—C=O, are the mandeloyl group of the formula

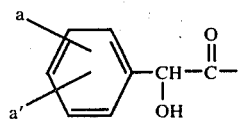

the O-formyl derivative thereof represented by the following formula

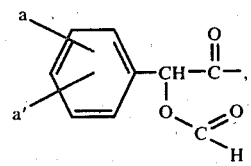

the α-carboxyphenylacetyl group represented by the following formula

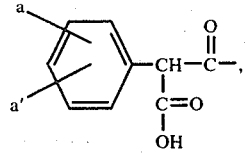

the α-sulfophenylacetyl group represented by the formula

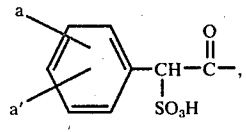

the phenylglycyl group represented by the formula

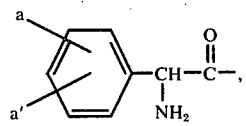

as well as those 2-thienyl and 3-thienyl acyl groups wherein the above formula the phenyl group is replaced with a 2-thienyl or 3-thienyl ring.

Illustrative of the foregoing acyl groups are 4-methylmandeloyl, 4-hydroxymandeloyl, 3-hydroxymandeloyl, 4-aminomandeloyl, 3-bromomandeloyl, 4-chloromandeloyl, 3-methyl-4-fluoromandeloyl, 2-fluoromandeloyl, 4-fluoromandeloyl, 4-methoxymandeloyl, 3,4-dimethyl-0-formylmandeloyl, 4-chloro-0-formylmandeloyl, 3-amino-0-formylmandeloyl, 3-bromo-0-formylmandeloyl, 3,4-dimethoxy-0-formylmandeloyl, 0-acetyl mandeloyl, 0-acetyl 4-hydroxymandeloyl, α-carboxy-4-methylphenylacetyl, α-carboxy-3,4-dichlorophenylacetyl, α-carboxy-4-hydroxyphenylacetyl, α-carboxy-2-methoxyphenylacetyl, α-carboxy-4-isopropoxyphenylacetyl, α-carboxy-3-hydroxyphenylacetyl, α-carboxy-4-aminophenylacetyl, α-sulfo-4-methylphenylacetyl, α-sulfo-3,4-dichlorophenylacetyl, α-formyloxy-2-thienylacetyl, α-sulfo-2-thienylacetyl, phenylglycyl, 4-hydroxyphenylglycyl, 3-chlorophenylglycyl, 3-hydroxyphenylglycyl, 4-methoxyphenylglycyl, α-amino-2-thienylacetyl, and α-amino-2-furylacetyl.

When in the foregoing formula R represents a group of the formula R'—CH₂—, illustrative of the acyl groups of the formula I are the following: 2-thienylacetyl, 3-thienylacetyl, 2-furylacetyl, oxazolyl-2-acetyl, thiazolyl-2-acetyl, and tetrazolyl-1-acetyl.

The sulfonate esters of this invention are prepared by reacting a 7-acylamido-3-hydroxy-3-cephem-4-carboxylic acid ester with a $C_1-C_6$ alkylsulfonyl halide, a phenylsulfonyl halide, or a substituted phenylsulfonyl halide at a temperature between about −5° and 35° C. in an aprotic solvent in the presence of a hydrogen halide acceptor. 7-Acylamido-3-hydroxy-3-cephem-4-carboxylic acid esters which can be used in the preparation are represented by the following formula II

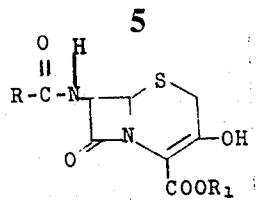

wherein R and $R_1$ have the same meanings as defined for formula I.

Representative of the alkyl and phenylsulfonyl halides which can be used are methanesulfonyl chloride, methanesulfonyl bromide, ethanesulfonyl chloride, n-butanesulfonyl chloride, n-hexanesulfonyl bromide, phenylsufonyl chloride, p-chlorophenylsulfonyl chloride, p-fluorophenylsulfonyl chloride, p-toluenesulfonyl chloride, p-toluenesulfonyl bromide, 3- or 4-nitrobenzenesulfonyl chloride or bromide, 3-ethylbenzenesulfonyl chloride and 3-bromobenzenesulfonyl chloride or bromide.

Aprotic solvents which can be employed are the ether solvents such as tetrahydrofuran, dioxane and the dimethyl ether of ethylene glycol or like ether solvents. A preferred solvent which can be used is dimethylacetamide.

The reaction is carried out in the presence of a hydrogen halide acceptor such as an unreactive tertiary amine such as triethylamine or pyridine or an alkylene oxide, for example, propylene or butylene oxide. The preferred hydrogen halide acceptor is propylene oxide. The tertiary amine type acceptors tend to cause isomerization of the 3-cephem to a 2-cephem compound. With an alkylene oxide such isomerization is kept to a minimum with most sulfonyl halides.

The reaction is carried out by the addition of the stoichiometric amount of the sulfonyl halide, or a slight excess thereof, to a solution of the 3-hydroxy-3-cephem ester in the aprotic solvent containing at least a stoichiometric amount of the hydrogen halide acceptor. The reaction mixture is stirred and preferably between about 10° and 25° C. for between 3 and 12 hours. The sulfonate ester product is recovered from the reaction mixture by extraction with an organic solvent such as ethyl acetate or methylene chloride and is recovered from the extract. The 3-sulfonate esters can be purified by chromatography over silica gel.

When the starting material contains a functional group in the 7-acylamido side chain which is capable of reacting with the sulfonyl halide, the reactive group is protected with a suitable protecting group. For example, the α-amino group of the phenylglycyl side chain can be protected during the sulfonyl ester formation with a variety of amino protecting groups. For example, the urethan protecting groups such as t-butyloxycarbonyl, 2,2,2-trichloroethoxycarbonyl, benzyloxycarbonyl, p-nitrobenzyloxycarbonyl, and the like; the enamine protecting groups formed with ethyl acetoacetate, acetyl acetone, and the like; the trityl group and other amino protectng groups. An amino substituent of a phenyl group in the 7 side chain can also be protected with the same groups. Likewise, an hydroxy group located in the 7-acylamido side chain, for example, in the mandeloyl side chain, is protected with a readily removable group such as, for example, the formyl group and the trichloroethoxycarbonyl group. Following the sulfonylation reaction such protecting groups are removed. Also, the $C_4$ carboxylic acid protecting group is removed to provide 3-sulfonyloxy-3-cephem-4-carboxylic acid antibiotic compound.

The foregoing description of the preparation of the sulfonate esters is illustrated in the following reaction scheme.

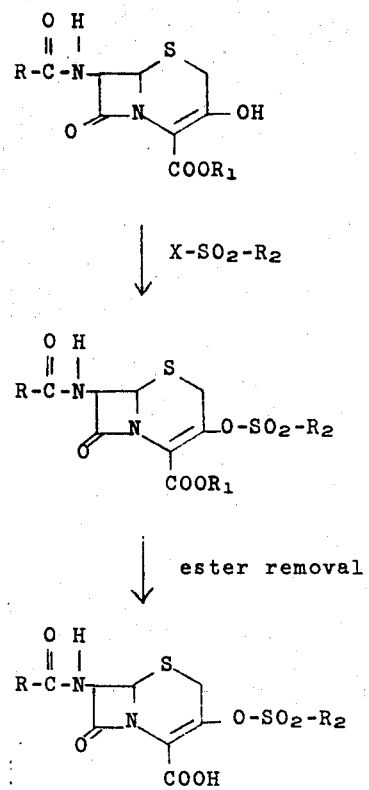

wherein R, $R_1$, and $R_2$ have the same meanings as previously defined.

In one embodiment of the invention, p-nitrobenzyl 7-(N-t-butyloxycarbonyl -D-phenylglycylamido)-3-hydroxy-3-cephem-4-carboxylate is reacted with methanesulfonyl chloride in dimethylacetamide in the presence of propylene oxide at about 5° C. to yield 7-(N-t-butyloxycarbonyl D-phenylglycylamido)-3-methylsulfonyloxy-0250 3-cephem-4-carboxylic acid p-nitrobenzyl ester. The product is hydrogenated over pre-reduced palladium on carbon catalyst in an inert solvent to effect removal of the p-nitrobenzyl ester group and the de-esterified product is then reacted with p-toluenesulfonic acid in acetonitrile to effect the removal of the t-butyloxycarbonyl group and provide the antibiotic 7-(D-phenylglycylamido)-3-methylsulfonyloxy-3-cephem-4-carboxylic acid.

The starting materials employed in the preparation of the compounds of the present invention are prepared as described in co-pending application Ser. No. 310,191 filed Nov. 28, 1972 now U.S. Pat. No. 3,917,587, 11-4-75. As described therein, a 7-acylamido-3-exomethylenecepham-4-carboxylic acid ester or a 7-amino-3-exomethylenecepham-4-carboxylic acid ester is reacted with ozone in an inert solvent at a temperature between −80° and 0° C. to form the ozonide derivative of the 3-exomethylene double bond. The ozonide intermediate, which is not isolated, is decomposed by reacting the ozonide in situ with a mild reducing agent such as sodium bisulfite, or preferably, sulfur dioxide, to provide the corresponding 3-hydroxy-3-cephem-4-carboxylic acid ester.

The ozonolysis of a 7-amino-3-exomethylenecepham-4-carboxylic acid ester or a 7-acylamido-3-exomethylenecepham-4-carboxylic acid ester of the following formula III is carried out by passing ozone through a solution of the 3-exomethylenecepham ester in an inert solvent at a temperature between about −80° and 0° C. The exomethylene double bond reacts with ozone to form in situ an intermediate ozonide which is decomposed, as hereinafter described, to form the 3-hydroxy-3-cephem ester of the formula IV.

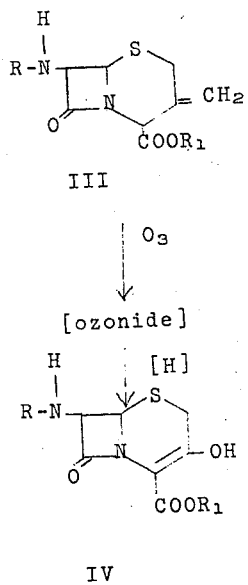

In the above formulae, R is hydrogen or an acyl group derived from a carboxylic acid and which acyl group is non-oxidizable under the described ozonolysis conditions. $R_1$ is an ester forming group and preferably one which is easily removed under hydrogenolysis, or acid or base hydrolysis conditions.

Ozone gas is prepared by means of an ozone generator of the type commonly used in synthetic and analytical chemical work to produce ozone by the action of an electric discharge on oxygen. One such ozone generator is that manufactured by the Welsback Corporation. The ozone is generated in a stream of oxygen which is then passed directly into the reaction vessel. The percentage of ozone contained in the oxygen stream can be varied as desired, for example, by varying the rate of flow of oxygen through the ozonizer as well as by varying the intensity of the electric discharge. The percentage of ozone in the oxygen stream can be determined iodometrically by titrating with sodium thoisulfate the amount of iodine liberated from a standard solution of potassium iodide by ozone from the generator. The percentage of ozone in the oxygen stream is not critical, however, for convenience in carrying out the ozonolysis method of this invention, an estimate of the amount of ozone flowing into the reaction mixture enables one to determine the time at which the desired reaction should be complete and thus minimizes the formation of over oxidation products.

Alternatively, the ozonolysis reaction can be followed chromatographically. For instance, a small aliquot of the reaction mixture is withdrawn, the ozonide decomposed, and the amount of unreacted starting material and 3-hydroxy-3-cephem product present in the sample is assessed by a comparison of the thin layer chromatogram with that of a known amount of starting material and a 3-hydroxy-3-cephem compound.

Inert solvents which can be used in the ozonolysis are those solvents in which the 3-exomethylene cepham esters are at least partially soluble and which are unreactive with ozone under the described conditions. Commonly used organic solvents such as methanol, ethanol, ethyl acetate, methyl acetate, and methylene chloride are satisfactory.

The concentration of the starting material in the inert solvent is not critical and it is preferred to use a solvent volume sufficient to form a complete solution.

The preferred temperature in the ozonolysis reaction is between about −80° and −50° C.

When ozonide formation is complete as determined by either method described above, any excess ozone present in the reaction mixture is purged from the mixture by bubbling nitrogen or oxygen through the mixture.

Following the removal of any excess ozone, the ozonide is decomposed by adding to the reaction mixture a mild reducing reagent selected from the group consisting of sodium bisulfite, sulfur dioxide, and trimethyl phosphite to provide the 3-hydroxy-3-cephem-4-carboxylic acid ester. The decomposition is carried out by adding an excess of the reducing reagent and then stirring the reaction mixture at a temperature of about −80° to 0° C. until the reaction mixture is negative in the potassium iodide-starch test.

A preferred reagent for decomposing the intermediate ozonide is gaseous sulfur dioxide. This reagent is preferred since it is completely volatilized from the reaction mixture during the subsequent work-up and thus does not complicate the recovery of the reaction product.

The 7-acylamido-3-hydroxy-3-cephem-4-carboxylic acid esters are recovered from the reaction mixture by first evaporating the mixture to dryness and thereafter extracting the product from the residue. Alternatively, N-acylated 3-hydroxy-3-cephem esters can be recovered from the organic liquid phase of the decomposition mixture by separating the liquid phase from insolubles, and after washing and drying, the organic layer is evaporated to yield the 3-hydroxy ester.

The 3-hydroxy nucleus ester, a 7-amino-3-hydroxy-3-cephem-4-carboxylic acid ester, is best isolated in the form of a salt as, for example, the hydrochloride or hydrobromide salt.

When an ester of 7-amino-3-exomethylenecepham-4-carboxylic acid (formula III, R=H) is ozonized, it is preferable to use a salt of this nucleus, for example, the hydrochloride or p-toluenesulfonate salt.

In a specific example of the preparation of a 3-hydroxy-3-cephem ester, p-methoxybenzyl 7-phenoxyacetamido-3-exomethylenecepham-4-carboxylate is dissolved in ethyl acetate and is reacted with ozone at a temperature of about −78° C. The excess ozone is expelled by bubbling oxygen through the cold solution. The ozonide is decomposed by adding excess sodium bisulfite to the reaction mixture at 0° C. with stirring. The organic layer is decanted from the insolubles and is washed, dried, and evaporated to yield p-methoxybenzyl 7-phenoxyacetamido-3-hydroxy-3-cephem-4-carboxylate.

In a further example, p-nitrobenzyl 7-amino-3-methylenecepham-4-carboxylate 1 hydrochloride is dissolved in methanol and ozone is bubbled through the solution at a temperature of about −78° C. Excess ozone is purged from the mixture with nitrogen and the ozonide is decomposed by bubbling sulfur dioxide through the mixture. The reaction mixture is evaporated to dryness and the residue, p-nitrobenzyl 7-amino-3-hydroxy-3-cephem-4-carboxylate is obtained as the hydrochloride salt.

The starting materials for the preparation of the 3-exomethylenecepham esters are prepared as described in copending application Ser. No. 118,941, filed Feb. 25, 1971, now U.S. Pat. No. 3,932,393 issued Jan. 13, 1976. As described therein, a 7-acylamido cephalosporanic acid is reacted with a sulfur containing nucleophile according to known procedures to effect the nucleophilic displacement of the acetoxy group of the cephalosporanic acid and provide a 7-acylamido-3-thiosubstituted-methyl-3-cephem-4-carboxylic acid. The 3-thiosubstituted cephem product is then reduced with hydrogen in the presence of Raney nickel or with zinc/-formic acid in the presence of dimethylformamide to produce the 3-exomethylenecepham acid. For example, 7-phenylacetamidocephalosporanic acid is reacted with potassium ethyl xanthate to yield 7-phenylacetamido-3-ethoxythionocarbonylthiomethyl-3-cephem-4-carboxylic acid which on reduction with zinc/formic acid in the presence of DMF yields 7-phenylacetamido-3-exomethylenecepham-4-carboxylic acid of the formula

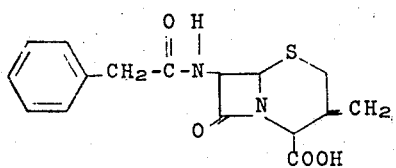

Likewise, there is described the 3-exomethylenecepham nucleus of the formula

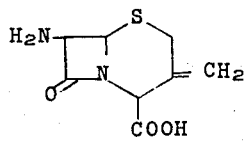

which can be prepared by reacting a 7-acylamido-3-exomethylenecepham-4-carboxylic acid ester with phosphorus pentachloride (PCl$_5$) in methylene chloride in the presence of pyridine to obtain the intermediate imino chloride. The imino chloride is reacted with methanol in the cold to afford the imino ether. The imino ether readily undergoes hydrolysis to provide the 7-amino-3-exomethylenecepham-4-carboxylic acid ester hydrochloride. The ester group is then removed to yield the 3-exomethylenecepham nucleus.

An ester of the 3-exomethylenecepham nucleus can be acylated with the desired derivative of a carboxylic acid to provide the 7-acylamido-3-exomethylenecepham-4-carboxylic acid ester and the acylated ester ozonized to the 3-hydroxy ester starting material of the formula II. Alternatively, an ester of the 3-hydroxy-7-amino-3-cephem nucleus can be acylated under non-anydydrous conditions to yield the 7-acylamido-3-hydroxy-3-cephem-4-carboxylic acid ester. The acylation of these nucleus esters is carried out under the conditions employed for the acylation of 7-aminocephalosporanic acid. However, in the acylation of a 7-amino-3-hydroxy-3-cephem ester, the acylation is preferably carried out in an aqueous medium, for example, in aqueous acetone or aqueous acetonitrile.

The 7-acylamido-3-alkyl- or phenylsulfonyloxy-3-cephem-4-carboxylic acid esters (formula I, R$_1$=ester) are useful as intermediates in the preparation of the free acid antibiotic forms of the compounds. Ester forming groups within the definition of R$_1$ are all known groups commonly employed to protect the C$_4$ carboxylic acid group of the cephalosporin molecule while reactions involving other groups in the molecule are performed. These ester forming groups are readily removed to provide the free acid by known reduction or hydrolysis procedures. For example, the p-nitrobenzyl ester group is removed via catalytic hydrogenolysis over palladium on carbon (U.S. Pat. No. 3,632,850); the diphenylmethyl group (benzhydryl) is removed with trifluoroacetic acid in anisole at about 10° C.; the p-methoxybenzyl group is removed with trifluoroacetic acid at about 10° C. [J. Org. Chem., 36, 1259 (1971)]; the 2,2,2-trichloroethyl group is removed with zinc and acid [J. Am. Chem. Soc. 88, 852 (1966)]; the benzyl ester group is removed via catalytic hydrogenolysis over palladium catalyst [U.S. Pat. No. 3,197,466, J. Org. Chem., 27, 1381 (1962)]; and the tert-butyl group is removed as described in J. Org. Chem., 31, 444 (1966).

In the preparation of the 3-sulfonate esters of this invention a minor amount of the corresponding 2-cephem isomer is sometimes formed. The preparation of the tosylate esters is generally accompanied by more isomerization to the 2-cephem isomer than with preparation of the alkylsulfonate esters. When the amount of 2-cephem-3-sulfonate ester formed in the sulfonylation reaction is significant, the mixture of 2- and 3-cephem sulfonates can be separated by chromatography over silica gel. Preferably, however, the isomer mixture is oxidized with a peracid such as m-chloroperbenzoic acid or peracetic acid to form the sulfoxides thereof. As is known in the art the sulfoxide formation of a 2-cephem is accompanied by isomerization to the 3-cephem isomer [J. Am. Chem. Soc., 35, 2430 (1970)]. The 3-cephem-3-sulfonate ester sulfoxide is then reduced to the sulfide, for example, with a phosphorus halide such as phosphorus trichloride according to the method described by U.S. Pat. No. 3,641,014. Accordingly, and 2-cephem isomeric product present in the desired 3-cephem-sulfonate ester can be converted to the desired 3-cephem isomer.

The 7-acylamido-3-cephem-3-sulfonate esters of the formula I wherein R$_1$ is hydrogen (the free acid form) are useful antibiotic substances which are useful in combatting infections attributable to gram-positive and gram-negative bacteria and also penicillin resistant staphylococci. The antibacterial activity of these sulfonate esters is illustrated by the following in vitro test data obtained with representative compounds. In Table I below, the minimum inhibitory concentration (MIC) for representative compounds against gram-negative bacteria is presented. The data were obtained by the standard Gradient-Plate method.

TABLE I

Antibiotic Activity of Cephalosporin Sulfonates
vs.
Gram-Negative Bacteria

| Test Organism | Test Compound[1] Minimum Inhibitory Concentration (mcg./ml.) | | | | | |
|---|---|---|---|---|---|---|
| | 1 | 2 | 3 | 4 | 5 | 6 |
| Shigella sp. | 10.7 | 7.0 | 6.5 | 19.5 | 16.5 | 13.6 |
| Escherichia coli | 11.0 | 13.1 | 8.8 | 16.3 | 24 | 19.5 |
| Klebsiella pneumoniae | 6.5 | 7.0 | 5.5 | 9.3 | 16.3 | 5.5 |
| Aerobacter aerogenes | 3.5 | 3.5 | 6.0 | 16.5 | 12.0 | 8.8 |
| Salmonella heidelberg | 2.0 | 4.0 | 6.0 | 125 | 13.5 | 7.0 |
| Pseudomonas aeruginosa | >200 | >200 | >200 | >200 | >200 | >200 |
| Serratia marcescens | 110 | 120 | 180 | >200 | >200 | 100 |

[1]Test compounds numbered 1–6 are as follows:
1 - 7-[2-(2-thienyl)acetamido]-3-methylsulfonyloxy-3-cephem-4-carboxylic acid.
2 - 7-[2-(2-thienyl)acetamido]-3-ethylsulfonyloxy-3-cephem-4-carboxylic acid.
3 - 7-[2-(2-thienyl)acetamido]-3-n-butylsulfonyloxy-3-cephem-4-carboxylic acid.
4 - 7-[2-(2-thienyl)acetamido]-3-(p-toluenesulfonyloxy)-3-cephem-4-carboxylic acid.
5 - 7-[2-(2-thienyl)acetamido]-3-(4-fluorobenzenesulfonyloxy)-3-cephem-4-carboxylic acid.
6 - 7-(D-phenylglycylamido)-3-methylsulfonyloxy-3-cephem-4-carboxylic acid.

In the same test method, the cephalosporin sulfonate esters inhibit the growth of clinical isolates of penicillin resistant Staphylococcus.

The 7-acylamido-3-cephem-3-sulfonate esters represented by the formula I when $R_1$ is hydrogen, form pharmaceutically acceptable salts with inorganic and organic bases. For example, the sodium, potassium, and calcium salts can be prepared with sodium carbonate, sodium bicarbonate, sodium hydroxide, potassium carbonate, and calcium hydroxide. Amine salts are formed with amines such as benzylamine, 2-aminoethanol, diethanolamine, diisopropylamine, and the like. Compounds of the formula I wherein R—C(O)— represents the phenylglycyl side chain form acid addition salts with suitable mineral and organic acids. For example, the hydrochloride, hydrobromide, and sulfate salts can be formed with hydrochloric, hydrobromic, and sulfuric acids. Likewise, the p-toluenesulfonate salt of the amine can be formed with p-toluenesulfonic acid. Such salts of the $C_4$ carboxyl group and an amino group of the $C_7$ side chain are useful in purifying the free acid form of the antibiotic and in preparing acceptable pharmaceutical formulations for administration.

The compounds of the formula I wherein $R_1$ is an ester group are useful intermidiates for preparing the free acid forms of the antibiotic.

Illustrative of the compounds of the invention represented by the formula I are

7-[2-(2-thienyl)acetamido]-3-methysulfonyloxy-3-cephem-4-carboxylic acid,

7-[2-(2-furyl)acetamido]-3-ethylsulfonyloxy-3-cephem-4-carboxylic acid, 7-phenylacetamido-3-(p-toluenesulfonyloxy)-3-cephem-4-carboxylic acid, 7-(4-chlorophenylmercaptoacetamido)-3-methylsulfonyloxy-3-cephem-4-carboxylic acid, 7-phenoxyacetamido-3-n-propylsulfonyloxy-3-cephem-4-carboxylic acid, 7-cyanoacetamido-3-methylsulfonyloxy-3-cephem-4-carboxylic acid, 7-(D-mandelamido)-3-methylsulfonyloxy-3-cephem-4-carboxylic acid, 7-(D-phenylglycylamido)-3-methylsulfonyloxy-3-cephem-4-carboxylic acid, 7-(D-4-hydroxyphenylglycylamido)-3-ethylsulfonyloxy-3-cephem-4-carboxylic acid, 7-(O-formyl D-mandelamido)-3-(p-toluenesulfonyloxy)-3-cehem-4-carboxylic acid, 7-(tetrazol-1-acetamido)-3-methylsulfonyloxy-3-cephem-4-carboxylic acid, 7-(5-amino-5-carboxyvaleramido)-3-(p-toluenesulfonyloxy)-3-cephem-4-carboxylic acid, 7-acetamido-3-benzenesulfonyloxy-3-cephem-4-carboxylic acid, 7-(α-sulfophenylacetamido)-3-ethylsulfonyloxy-3-cephem-4-carboxylic acid, 7-(α-carboxy-4-chlorophenylacetamido)-3-n-butylsulfonyloxy-3-cephem-4-carboxylic acid, and the pharmaceutically acceptable non-toxic salts thereof.

This invention is further illustrated by the following examples of the preparation of starting materials and compounds of the invention.

A. PREPARATION OF STARTING MATERIALS

EXAMPLE 1 p-Nitrobenzyl 7-amino-3-methylenecepham-4-carboxylate hydrochloride

To a solution of 965 mg. (2 mmole) of p-nitrobenzyl 7-phenoxyacetamido-3-methylenecepham-4-carboxylate in 10 ml. of methylene chloride were added 175 mg. of dry pyridine and 460 mg. of phosphorus pentachloride and the mixture was stirred at room temperature for 6 hours. One ml. of isobutanol was added to the mixture which was then stored at 0° C. overnight. The reaction product, p-nitrobenzyl 7-amino-3-methylenecepham-4-carboxylate hydrochloride, which formed as a crystalline precipitate was filtered to yield 430 mg. (58 per cent yield).

Elemental Analysis for $C_{15}H_{16}N_3O_5SCl$: Theory: C, 46.69; H, 4.18; N, 10.89. Found: C, 46.40; H, 4.20; N, 10.62.

I.R. (Nujol Mull): Carbonyl absorption at 5.65 (β-lactam) and 5.75 (ester) microns.

N.M.R. (DMSO $d_6$) signals at 6.34 (2d, 2H, $C_2$—$H_2$), 4.98 (d, 1H, $C_6$—H); 4.7—4.4 (m, 6H, $C_4$13 H, ester $CH_2$, $C_4$—$CH_2$ and $C_7$—H); and 2.4—1.6 (m, 4H, aromatic H) tau.

EXAMPLE 2 p-Nitrobenzyl 7-amino-3-hydroxy-3-cephem-4-carboxylate hydrochloride

A solution of 4 g. of p-nitrobenzyl 7-amino-3-methylenecepham-4-carboxylate hydrochloride in 620 ml. of methanol was cooled in a dry ice-acetone bath and ozone was bubbled through the cold solution for about 20 minutes. The reaction mixture was purged of the remaining ozone by passing nitrogen through the solution and 10 g. of sodium bisulfite were added.

The reaction mixture was stirred for one hour at ice-bath temperature at which time the mixture gave a negative potassium iodide starch test.

The mixture was evaporated in vacuo to yield the reaction product as an amorphous yellow residue. The residue was crystallized in acetone to yield 3.4 g. of p-nitrobenzyl 7-amino-3-hydroxy-3-cephem-4-carboxylate hydrochloride as a crystalline acetone solvate.

I.R. (Nujol Mull): Carbonyl absorption bands at 5.60 ($\beta$-lactam) and 6.04 (ester carbonyl hydrogen bonded to 3 hydroxy) microns.

N.M.R. (DMSO $d_6$) signals at 7.92 (s, 3H, ½ mole acetone), 6.22 (2d, 2H, $C_2$—$H_2$), 5.07 (d, 1H, $C_6H$), 4.8–4.5 (m, 3H, ester $CH_2$ and $C_7H$), 2.4–1.6 (m, 4H, aromatic H) tau.

EXAMPLE 3 p-Nitrobenzyl 7-[2-(2-thienyl)acetamido]-3-hydroxy-3-cephem-4-carboxylate to a solution of 1.55 g. of p-nitrobenzyl 7-amino-3-hydroxy-3-cephem-4-carboxylate hydrochloride in 30 ml. of acetone containing 364 mg. (0.5 ml., 3.6 mmole) of triethylamine was added 962 mg. of urea. With stirring at room temperature, a solution of 730 mg. (4.4 mmole) of 2-thiophene acetyl chloride in 20 ml. of acetone was added dropwise to the mixture. After 2.5 hours the reaction mixture was filtered and evaporated. The residue was dissolved in ethyl acetate and the solution was washed successively with water, a 5 percent solution of sodium bicarbonate, 5 percent hydrochloric acid, and a saturated solution of sodium chloride. The washed solution was dried and then was concentrated by evaporation in vacuo to yield 1.2 g. of the reaction product as a crystalline residue. The product was recrystallized from ethyl acetate to yield pure p-nitrobenzyl 7-[2-(2-thienyl)acetamido]-3-hydroxy-3-cephem-4-carboxylate having the following spectral properties.

I.R. (Nujol Mull): Absorption peaks at 3.0 (amide NH), 5.68 ($\beta$-lactam carbonyl), and 6.1 (amide, and ester hydrogen bonded to 3 OH) microns.

N.M.R. (CDCl$_3$/DMSO $d_6$):signals at 6.54 (2d, 2H, $C_2H_2$), 6.16 (s, 2H, side-chain $CH_2$), 4.90 (d, 1H, $C_6H$), 4.60 (d, 2H, ester $CH_2$), 4.43 (q, 1H, $C_7H$), 3.1–1.6 (m, 7H, aromatic H), and 1.30 (d, 1H, amide NH) tau.

B. PREPARATION OF SULFONATE ESTERS

EXAMPLE 4 p-Nitrobenzyl 7-[2-(2-thienyl)acetamido]-3-methylsulfonyloxy-3-cephem-4-carboxylate To a solution of 4.75 g. (10 mmole) of p-nitrobenzyl 7-[2-(2-thienyl)acetamido]-3-hydroxy-3-cephem-4-carboxylate in 50 ml. of dry dimethylacetamide were added 2 ml. of propylene oxide. To the solution was added with stirring one equivalent of methanesulfonyl chloride and stirring was continued for 3 hours. The reaction mixture was then taken up in ethyl acetate and the solution was washed with a saturated solution of sodium chloride. The washed organic phase was evaporated in vacuo to dryness to obtain the reaction product mixture as a residue. The reaction product was purified by preparative thin layer chromatography on silica gel using for elution 65 percent ethyl acetate/hexane.

The purified product gave the following percent elemental composition on microanalysis.

Calculated for $C_{21}H_{19}N_3O_9S_3$: Theory: C, 45.56; H, 3.46; N, 7.59; S, 17.38. Found: C, 45.74; H, 3.56; N, 7.30; S, 17.06.

The nuclear magnetic resonance spectrum and the infrared absorption spectrum were in agreement with the structure of the product formed.

N.M.R. (DMSO $d_6$) delta values: 3.47 (s, 3H, methyl); 3.80 (broad s, 2H, side chain $CH_2$); 3.91 (q, 2H, $C_2H_2$); 5.29 (d, 1H, $C_6H$); 5.46 (broad s, 2H, ester $CH_2$); 5.84 (q, 1H, $C_7H$); 6.86–7.44 (m, 3H, thiophene); and 7.98 (q, 4H, phenyl).

I.R. (mull) 1785, 1350, and 1158 cm$^{-1}$

U.V. (Ethanol) $\lambda$ max 264 m$\mu$.

The above product (2 g.) was dissolved in a solvent mixture of 15 ml. of methanol and 20 ml. of tetrahydrofuran and 3 g. of prereduced 5 percent palladium on carbon catalyst were added. (The catalyst had been prereduced in 15 ml. of methanol for 1 hour prior to use.) The mixture was hydrogenated for 1.5 hours during which time the theoretical hydrogen uptake had occurred.

The catalyst was filtered and the filtrate was evaporated to dryness on a rotary evaporator in vacuo. The residue was dissolved in 20 ml. of ethyl acetate and 20 ml. of cold water were added. The pH of the solution was adjusted to pH 7 with a solution of sodium bicarbonate and the organic layer was separated. Ethyl acetate was layered over the aqueous phase and the pH adjusted to 2.0 with 1N hydrochloric acid. The organic layer was separated and combined with an ethyl acetate extract of the acidified aqueous layer. The combined extract and organic layer were dried over magnesium sulfate and evaporated to dryness to yield the de-esterified product, 7-[2-(2-thienyl)acetamido]-3-methylsulfonyloxy-3-cephem-4-carboxylic acid.

N.M.R. (acetone $d_6$) delta values: 3.33 (s, 3H, methyl); 3.50–4.00 (m, 4H, two $CH_2$); 5.10 (d, 1H, $C_6H$); 5.88 (d, 1H, $C_7H$); 6.80–7.40 (m, 3H, thiophene).

I.R. (KBr) 1795, 1175 cm$^{-1}$

U.V. (Ethanol) $\lambda$ max 265 m$\mu$. (shoulder)

Electrometric titration (80 percent aqueous methyl cellosolve) $pK_a$ 3.9.

EXAMPLE 5

7-[2-(2-Thienyl)acetamido]-3-ethylsulfonyloxy-3-cephem-4-carboxylic acid

By following the procedure described by Example 4, 4.7 g. (10 mmole) of p-nitrobenzyl 7-[2-(2-thienyl)acetamido]-3-hydroxy-3-cephem-4-carboxylate was reacted for about 3 hours in 50 ml. of dimethylacetamide containing about 2 ml. of propylene oxide with a stoichiometric amount of ethanesulfonyl chloride. The reaction mixture was dissolved in ethyl acetate and the solution washed with a saturated solution of sodium chloride. The organic phase was dried and evaporated to dryness to provide the reaction product. The product was purified by preparative thin layer chromatography on silica gel by employing 65 percent ethyl acetate/hexane for development. The purified product, p-nitrobenzyl 7-[2-(2-thienyl)acetamido]-3-ethylsulfonyloxy-3-cephem-4-carboxylate, gave the following percent elemental composition on microanalysis for the formula $C_{22}H_{21}N_3O_9S_3$:

Theory: C, 46.55; H, 3.73; N, 7.40; S, 16.95 Found: C, 46.32; H, 3.48; N, 7.5; S, 16.67.

I.R. (chloroform) 1800, 1358, 1163 $Cm^{-1}$

U.V. (ethanol) λ max 265 mμ.

N.M.R. ($CDCl_3$) delta values: 1.47 (T, 3H, methyl); 3.40 (q, 2H, $CH_2$); 3.73 (q, 2H, $C_2$—$CH_2$); 3.88 (s, 2H side chain $CH_2$); 5.13 (d, 1H, $C_6H$); 5.20 (s, 2H, ester $CH_2$); 5.91 (q, 1H, $C_7H$); 6.85 (d, 2H, NH); 7.00–7.44 (m, 3H, thiophene); 7.96 (q, 4H, phenyl).

The above product was hydrogenated to effect removal of the p-nitrobenzyl ester group by following the hydrogenation method described in Example 4, to provide 7-[2-(2-thienyl)acetamido]-3-ethylsulfonyloxy-3-cephem-4-carboxylic acid.

N.M.R. ($CDCl_3$+ acetone $d_6$) delta values: 1.45 (T, 3H, methyl); 3.41 (q, 2H, $CH_2$); 3.69 (q, 2H, ring $CH_2$); 3.84 (s, 2H, side chain $CH_2$); 5.12 (d, 1H, $C_6$—H); 5.83 (q, 1H, $C_7$—H); 6.88–7.32 (m, 3H, thiophene).

I.R. (mull) 1787, 1350 and 1170 $cm^{-1}$

Electrometric titration in 80 percent aqueous methyl cellosolve $pK_a$ 4.15.

EXAMPLE 6

7-[2-(2-Thienyl)acetamido]-3-n-butylsulfonyloxy-3-cephem-4-carboxylic acid

By following the esterification procedure of Example 4, 4.7 g. of p-nitrobenzyl 7-[2-(2-thienyl)acetamido]-3-hydroxy-3-cephem-4-carboxylate was reacted with the stoichiometric amount of n-butylsulfonyl chloride in dimethylacetamide containing propylene oxide to provide 2.1 g. of the 3-n-butylsulfonyloxy derivative.

Percent elemental composition for $C_{24}H_{25}N_3O_9S_3$: Theory: C, 48.39; H, 4.23; N, 7.05. Found: C, 47.94; H, 4.27; N, 6.31.

N.M.R. (DMSO $d_6$) delta values: 0.87 (t, 3H, methyl); 1.10–1.90 (m, 4H, two $CH_2$); 2.45–2.87 (m, 2H, $CH_2$); 3.71 (q, 2H, ring $CH_2$); 3.79 (s, 2H, side chain $CH_2$); 5.28 (d, 1H, $C_6H$); 5.42 (broad s, 2H, ester $CH_2$); 5.82 (q, 1H, $C_7H$); 6.50–6.97 (m, 3H, thiophene); 8.07 (q, 4H, phenyl).

I.R. ($CHCl_3$) 1801, 1355, 1170 $cm^{-1}$

The p-nitrobenzyl ester group is removed from the above n-butylsulfonyl derivative by following the hydrogenolysis method described by Example 4 to provide 7-[2-(2-thienyl)-acetamido]-3-n-butylsulfonyloxy-3-cephem-4-carboxylic acid.

N.M.R. ($CDCl_3$) delta values: 0.98 (t, 3H, methyl); 1.10–2.00 (m, 4H, two $CH_2$); 2.65–3.00 (m, 2H, $CH_2$); 3.60–4.10 (m, 4H, $C_2$ and side chain $CH_2$); 5.09 (d, 1H, $C_6H$); 5.78 (q, 1H, $C_7H$); 6.85–7.38 (m, 3H, thiophene).

I.R. $CHCl_3$) 1787, 1360 $cm^{-1}$

Electrometric titration in 80 percent aqueous methyl cellosolve $pK_a$ 4.75.

EXAMPLE 7

7-[2-(2-Thienyl)acetamido]-3-(p-toluenesulfonyloxy)-3-cephem-4-carboxylic acid

To a solution of 9.5 g. (20 mmole) of p-nitrobenzyl 7-[2-(2-thienyl)acetamido]-3-hydroxy-3-hydroxy-3-cephem-4-carboxylate in 30 ml. of DMAC and 30 ml. of propylene oxide maintained at ice-bath temperature were added 4.2 g. (22 mmole, 1.1 equivalents) of P-toluenesulfonyl chloride. The reaction mixture was stirred at ice-bath temperature for about 15 hours and then for about 3 hours at room temperature. Thereafter, the reaction mixture was evaporated to remove excess propylene oxide and the concentrate was dissolved in ethyl acetate. The solution was washed with a saturated sodium chloride solution and dried. Evaporation of the dried solution under reduced pressure afford the crude tosylate ester as a dry residue. The residue was dissolved in ethyl acetate and chromatographed over water-deactivated silica gel (Woelm silica gel, 10 percent water deactivated) packed in a glass column. The column was eluted with 45 percent by volume of hexane in ethyl acetate. Four fractions of approximately 100 ml. volume were collected. Fractions 2 and 3 were combined and evaporated under reduced pressure to yield 4.75 g. of p-nitrobenzyl 7-[2-(2-thienyl)acetamido]-3-(p-toluenesulfonyloxy)-3-cephem-4-carboxylate mixed with the corresponding 2-cephem isomer.

To a solution of 1.26 g. of the isomeric mixture in 20 ml. of methylene chloride maintained at ice-bath temperature was added a solution of 0.4 g. of m-chloroperbenzoic acid in 20 ml. of methylene chloride. The mixture was stirred for 40 minutes and was evaporated to dryness. The residue was triturated with iso-propanol, filtered, washed with ether and dried to yield 1.1 g. of product, p-nitrobenzyl 7-[2-(2-thienyl)acetamido]-3-(p-toluenesulfonyloxy)-3-cephem-4-carboxylate sulfoxide. Percent elemental composition of the sulfoxide product, calculated for $C_{27}H_{23}N_3O_{10}S_3$, was as follows:

Theory: C, 50.23; H, 3.59; N, 6.51. Found: C, 49.98; H. 3.30; N, 6.53.

The $\Delta^3$-cephem sulfoxide was reduced to the $\Delta^3$-cephem sulfoxide as follows:

To a solution of 1.0 g. of the sulfoxide in 25 ml. of acetonitrile containing 5 ml. of DMF maintained at ice-bath temperature were added 0.157 g. of phosphorus tribromide with stirring. The reaction mixture was stirred for 1 hour in the cold. Ethyl acetate and a saturated aqueous sodium chloride solution were added to the mixture. the product was extracted with the ethyl acetate and the organic layer was washed 3 times with a saturated sodium chloride solution. The organic phase was dried and evaporated to yield 1.1 g. of the product, p-nitrobenzyl 7-[2-(2-thienyl)acetamido]-3-(p-toluenesulfonyloxy)-3-cephem-4-carboxylate.

The above product was hydrogenated over prereduced 5 percent palladium on carbon catalyst in methanol-THF by the procedure described in Example 4 to provide the free carboxylic acid product, 7-[2-(2-thienyl)acetamido]-3-(p-toluenesulfonyloxy)-3-cephem-4-carboxylic acid.

N.M.R. ($CDCl_3$) delta values: 2.47 (s, 3H, methyl); 3.40–4.10 (m, 4H, $C_2$ and side chain $CH_2$); 5.05 (d, 2H, $C_6H$); 5.80 (q, 1H, $C_7$—H); 6.85–7.38 (m, 3H, thiophene); 7.61 (q, 4H, phenyl).

I.R. ($CHCl_3$) 1790, 1380, 1170 $Cm^{-1}$

Electrometric titration (80 percent aqueous methyl cellosolve) $pK_a$ 4.4.

U.V. (ethanol) λ max 265 mμ. (shoulder).

EXAMPLE 8

7-[2-(2-Thienyl)acetamido]-3-(4-fluorobenzenesulfonyloxy)-3-cephem-4-carboxylic acid By following the sulfonation and de-esterification procedures described in Example 4 p-nitrobenzyl 7-[2-(2-thienyl)acetamido]-3-hydroxy-3-cephem-4-carboxylate was reacted with 4-fluorobenzenesulfonyl chloride in DMAC in the presence of propylene oxide and the recovered sulfonation product, p-nitrobenzyl 7-[2-(2-thienyl)acetamido]-3-(4-fluorobenzenesulfonyloxy)-3-cephem-4-carboxylate was hydrogenated in methanol-THF over prereduced 5 percent palladium on carbon catalyst to provide the product, 7-[2-(2-thienyl)acetamido]-3-(4-fluorobenzenesulfonyloxy)-3-cephem-4-carboxylic acid.

Percent elemental analysis obtained on microanalysis for $C_{19}H_{15}N_2O_7S_3F$: Theory: C, 45.78; H, 3.03; N, 5.62; F, 3.81. Found: C, 5.77 46.04; H, 3.31; N, 5.33; F, 3.89. m,

N.M.R. (CDCl$_3$) delta values: 3.48–4.10 (broad $m$, 4H, $C_2$ and side chain CH$_2$); 5.05 ($d$, 1H, $C_6$—H); 5.77 ($q$, 1H, $C_7$—H); 6.80–7.48 and 7.77–8.16 (broad $m$, 7H, thiophene and phenyl H).

I.R. (CHCl$_3$) 1792, 1385, and 1160 cm$^{-1}$

Electrometric titration (80 percent aqueous methyl cellosolve) $pK_a$ 4.25.

EXAMPLE 9

To a solution of 11.1 g. of p-nitrobenzyl 7-amino-3-hydroxy-3-cephem-4-carboxylate hydrochloride in 500 ml. of tetrahydrofuran were added 15.1 g. of sodium bisulfite. The mixture was stirred at room temperature for 1 hour and 6.4 g. of N-(t-butyloxycarbonyl)-phenylglycine and 6.25 g. of N-ethoxycarbonyl-2-ethoxy-1,2-dihydroquinoline (EEDQ) were then added. The reaction mixture was stirred at room temperature for 7 hours after which the mixture was evaporated to remove tetrahydrofuran. The concentrate was dissolved in ethyl acetate and the solution was washed consecutively with a solution of sodium bicarbonate, dilute hydrochloric acid and a saturated sodium chloride solution and was dried. The dried solution was evaporated to dryness to yield 11.14 g. of p-nitrobenzyl 7-(N-t-butyloxycarbonyl-d-phenylglycylamido)-3-hydroxy-3-cephem-4-carboxylate.

To a solution of 11.14 g. of the above product in 50 ml. of DMAC containing 25 ml. of propylene oxide were added at room temperature 1.47 ml. of methanesulfonyl chloride. After the mixture was stirred for about 3 hours, an additional 1.47 ml. of methanesulfonyl chloride were added and the mixture was stirred for an additional 15 hours. The reaction mixture was diluted with ethyl acetate and the solution extracted 4 times with a saturated solution of sodium chloride. The washed organic phase was dried and evaporated to dryness to yield crude reaction product, p-nitrobenzyl 7-(N-t-butyloxycarbonyl-D-phenylglycylamido)-3-methylsulfonyloxy-3-cephem-4-carboxylate. The product was purified by dissolution in methylene chloride and precipitation from solution on dilution with hexane. The purified product, 8.09 g. was filtered and dried.

The p-nitrobenzyl ester group was removed by hydrogenation of the product over pre-reduced 5 percent palladium on carbon by the method described in Example 4, to yield 4.21 g. of the free acid.

The free acid obtained, 1.545 g. was dissolved in 3 ml. of dry acetonitrile and 1.7 g. of p-toluenesulfonic acid were added. The reaction mixture was stirred overnight at room temperature. Water was added to the mixture and the pH adjusted to 5.0 with a solution of sodium bicarbonate. The mixture was then evaporated to remove acetonitrile and the aqueous residue was filtered. The pH of the filtrate was adjusted to pH 4.0 and was then freeze dried. The freeze dried mixture was triturated with acetone and filtered. The solid was dissolved in 15 ml. of water and about 5 ml. of acetone were added to the solution at ice-bath temperature. The product, 7-(D-phenylglycylamido)-3-methylsulfonyloxy-3-cephem-4-carboxylic acid, crystallized from the cold solution and was filtered, washed with cold water and with acetone and was dried to provide 143 mg.

Percent elemental composition for $C_{16}H_{17}N_3O_7S_2$: Theory: C, 44.92; H, 4.01; N, 9.83. Found: C, 44.13; H, 4.24; N, 9.26.

Electrometric titration in 80 percent aqueous methyl cellosolve $pK_a$ 3.6 and 6.75

I.R. (mull) 1780, 1360, and 1178 cm$^{-1}$

U.V. (pH 6 buffer) λ max 261 mμ. ($\epsilon$=8400)

N.M.R. (DMSO $d_6$) delta values: 3.28 ($s$, 3H, methyl); 3.55 ($q$, 2H, $C_2$—CH$_2$); 4.92–5.1 ($m$, 2H, $C_6$H and CH of side chain); 5.68 ($q$, 1H, $C_7$—H); 7.48 ($m$, 5H, phenyl).

I claim:

1. A 3-cephem-3-sulfonate ester of the formula

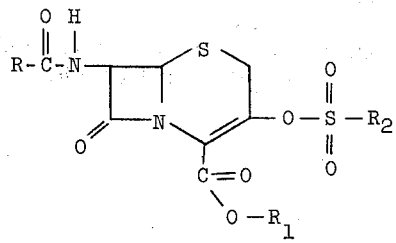

wherein R is $C_1$–$C_6$ alkyl, $C_1$–$C_3$ haloalkyl, $C_1$–$C_3$ cyanoalkyl, phenyl, methylphenyl, hydroxyphenyl, halophenyl, nitrophenyl, aminophenyl, methoxyphenyl, 4-amino-4-carboxybutyl, or a 4-substituted-amino-4-carboxybutyl ester group of the formula

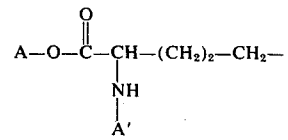

wherein A is diphenylmethyl, p-nitrobenzyl, benzyl, 2,2,2-trichloroethyl, t-butyl, or p-methoxybenzyl and A' is $C_2$–$C_4$ alkanoyl, $C_2$–$C_4$ haloalkanoyl, benzoyl, nalobenzoyl, 2,4-dinitrophenyl, or phthaloyl; or R is a group of the formula

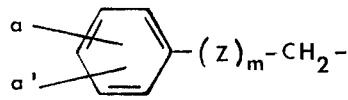

wherein a and a' independently are hydrogen, $C_1$–$C_4$ lower alkyl, $C_1$–$C_4$ lower alkoxy, halogen, hydroxy, nitro, amino, or carboxy;
Z is O or S; and
$m$ is 0 or 1;
or R is a group of the formula

wherein P is 2-thienyl, 3-thienyl, phenyl or a substituted phenyl group of the formula

wherein $a$ and $a'$ are as defined above, Q is hydroxyl, formyloxy, acetoxy, carboxy, sulfo, amino, or amino protected by t-butyloxycarbonyl, 2,2,2-trichloroethoxycarbonyl, benzyloxycarbonyl, p-nitrobenzyloxycarbonyl or by an enamine formed with ethyl acetoacetate or acetylacetone;
or R is a group of the formula

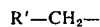

wherein R' is 2-thienyl, 3-thienyl, 2-furyl, 2-oxazolyl, 2-thiazolyl or 1-tetrazolyl
$R_2$ is $C_1$–$C_6$ alkyl, phenyl, halophenyl, $C_1$–$C_3$ lower alkylphenyl, or nitrophenyl;
$R_1$ is hydrogen, benzyl, 4-methoxybenzyl, 4-nitrobenzyl, diphenylmethyl, 2,2,2-trichloroethyl or t-butyl;
and when $R_1$ is hydrogen the pharmaceutically acceptable non-toxic salts thereof.

2. The compound of claim 1 wherein R is a group of the formula

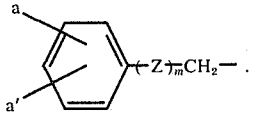

3. The compound of claim 1 wherein R is a group of the formula

4. The compound of claim 3 wherein P is phenyl and Q is amino.

5. The compound of claim 4, said compound being 7-(D-phenylglycylamido)-3-methylsulfonyloxy-3-cephem-4-carboxylic acid.

6. The compound of claim 1 wherein R is a group of the formual

7. The compound of claim 6 wherein R' is 2-thienyl.

8. The compound of claim 7 wherein $R_2$ is $C_1$–$C_6$ alkyl.

9. The compound of claim 8, said compound being 7-[2-(2-thienyl)acetamido]-3-methylsulfonyloxy-3-cephem-4-carboxylic acid.

10. The compound of claim 7 wherein $R_2$ is phenyl, halophenyl or $C_1$–$C_3$ lower alkylphenyl.

11. The compound of claim 10, said compound being 7-[2-(2-thienyl)acetamido]-3-(p-toluenesulfonyloxy)-3-cephem-4-carboxylic acid.

* * * * *